United States Patent [19]
Stoltefuss et al.

[11] Patent Number: 5,508,406
[45] Date of Patent: Apr. 16, 1996

[54] QUINOLYL-DIHYDROPYRIDINE ESTERS, PROCESSES FOR THEIR PREPARATION, AND THEIR USE IN MEDICAMENTS

[75] Inventors: Jürgen Stoltefuss, Haan; Siegfried Goldmann; Alexander Straub, both of Wuppertal; Martin Bechem, Wuppertal; Rainer Gross, Wuppertal; Siegbert Hebisch, Bottrop; Joachim Hütter, Wuppertal; Howard-Paul Rounding, Wuppertal, all of Germany

[73] Assignee: Bayer Aktiengesellschaft, Leverkusen, Germany

[21] Appl. No.: 230,266

[22] Filed: Apr. 20, 1994

[30] Foreign Application Priority Data

Apr. 27, 1993 [DE] Germany .......................... 43 13 697.4

[51] Int. Cl.⁶ ...................... C07D 401/04; C07D 401/14; A61K 31/47
[52] U.S. Cl. ...................... 514/314; 546/115; 546/167
[58] Field of Search ...................... 546/115, 167; 514/413

[56] References Cited

U.S. PATENT DOCUMENTS

| | | | |
|---|---|---|---|
| 4,145,432 | 3/1979 | Sato | 260/295.5 R |
| 4,248,873 | 2/1981 | Bossert et al. | 424/256 |
| 5,100,900 | 3/1992 | Stoltefuss et al. | 514/314 |
| 5,204,472 | 4/1993 | Stoltefuss et al. | 546/165 |

FOREIGN PATENT DOCUMENTS

| | | |
|---|---|---|
| 0071819 | 2/1982 | European Pat. Off. . |
| 0451654 | 10/1991 | European Pat. Off. . |
| 0452712 | 10/1991 | European Pat. Off. . |
| 0538690 | 4/1992 | European Pat. Off. . |
| 0515940 | 12/1992 | European Pat. Off. . |
| 0518105 | 12/1992 | European Pat. Off. . |

OTHER PUBLICATIONS

P. G. Baraldi, et al., Collect Czech Chem. Commun. "Synthesis and Calcium Antagonist Activity of Dialkykl 1,4–Dimethyl–4–(Nitrogenous Heteroaryl)–3,5–Pyridine Dicarboxylates," vol. 57, pp. 169–178 (1992).

*Primary Examiner*—David B. Springer
*Attorney, Agent, or Firm*—Sprung Horn Kramer & Woods

[57] ABSTRACT

The invention relates to new 4-quinolyl-dihydropyridine esters of the general formula (I)

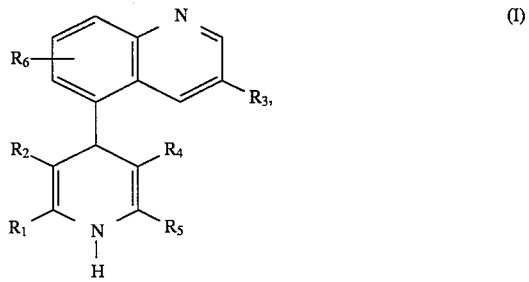

in which $R_1$ to $R_6$ have the meaning given in the description, to processes for their preparation and to their use in medicaments, especially in agents for the treatment of cardiac circulatory disorders.

7 Claims, No Drawings

QUINOLYL-DIHYDROPYRIDINE ESTERS, PROCESSES FOR THEIR PREPARATION, AND THEIR USE IN MEDICAMENTS

The invention relates to new 4-quinolyl-dihydropyridine esters, to processes for their preparation and to their use in medicaments, especially in agents for the treatment of cardiac circulatory disorders.

It is already known that 1,4-dihydropyridines possess vasodilatory properties and can be used as coronary agents and antihypertensives. It is also known that 1,4-dihydropyridines inhibit the contractility of smooth and cardial muscles and can be employed for the treatment of coronary and vascular disorders. In addition, from U.S. Pat. No. 5,100,900, 4-quinolyl-dihydropyridines possessing a positively inotropic action are already known.

Given the knowledge of the prior art, it was unforeseeable that the compounds according to the invention would possess a contractility-increasing action which is positively inotropic with respect to the cardiac muscle, while having a largely neutral vascular behaviour.

The present invention relates to new 4-quinolyl-dihydropyridine esters of the general formula (I)

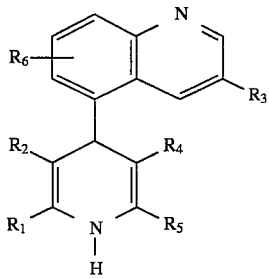

in which
$R^1$ and $R^5$ are identical or different and represent straight-chain or branched alkyl having up to 8 carbon atoms,
$R^2$ represents nitro or cyano
or
$R^1$ and $R^2$ together form a lactone ring of the formula

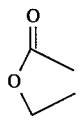

in which
$R^6$ represents hydrogen, halogen or straight-chain or branched alkyl or alkoxy having in each case up to 8 carbon atoms,
$R^5$ represents aryl having from 6 to 10 carbon atoms which is optionally substituted up to 2 times by identical or different substituents comprising halogen, nitro, cyano, hydroxyl, trifluoromethyl, trifluoromethoxy, trifluoromethylthio, straight-chain or branched alkyl, alkoxy or alkoxycarbonyl having in each case up to 8 carbon atoms, or carboxyl, or represents thienyl or pyridyl which are optionally substituted by halogen,
$R^4$ represents cyano, nitro or formyl
or
$R^4$ and $R^5$ together form a lactone ring of the formula

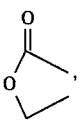

or
$R^4$ represents a group of the formula —CO—A—$R^8$ or —CO—N$R^9R^{10}$
in which
A denotes a direct bond or an oxygen atom,
$R^8$ denotes cycloalkyl having from 3 to 8 carbon atoms which is optionally interrupted by the group —$NR^{11}$, or denotes a straight-chain, branched, cyclic, saturated or unsaturated hydrocarbon radical having up to 12 carbon atoms which is optionally interrupted by oxygen,

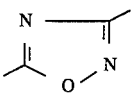

or by arylidene having from 6 to 10 carbon atoms, where the arylidene is optionally substituted by halogen, nitro, amino, hydroxyl or carboxyl or by straight-chain or branched alkyl, alkoxy or alkoxycarbonyl having in each case up to 8 carbon atoms or the hydrocarbon radical is optionally substituted or replaced by phenyl which may in turn be substituted by fluorine, chlorine, methyl or methoxy, or the hydrocarbon radical is optionally interrupted by a group of the formula —$S(O)_a$ or —$NR^{11}$,
a denotes the number 0, 1 or 2
and
$R^{11}$ denotes hydrogen or aryl having from 6 to 10 carbon atoms which is optionally substituted by halogen, nitro, phenyl or straight-chain or branched alkyl or alkoxy having in each case up to 4 carbon atoms, or denotes straight-chain or branched alkyl having up to 6 carbon atoms or cycloalkyl having from 3 to 8 carbon atoms, both alkyl and cycloalkyl being optionally substituted by aryl having from 6 to 10 carbon atoms,
and where the hydrocarbon radical, in the case
where A represents oxygen, is always mono- or disubstituted by identical or different substituents comprising cycloalkyl having from 3 to 8 carbon atoms or by —CO—$NR^{12}R^{13}$, —$NR^{14}$—CO—$R^{15}$, —$NR^{16}$—$SO_2$—$R^{17}$, —$SO_2$—$NR^{18}R^{19}$, O—$NO_2$, —O—$(CH_2)_b$—$R^{20}$, —$S(O)_c$—$(CH_2)_d$—$R^{21}$, —$NR^{22}R^{23}$ or —$NR^{24}COOR^{25}$,
in which
$R^{12}$, $R^{13}$, $R^{14}$, $R^{15}$, $R^{16}$, $R^{17}$, $R^{18}$, $R^{19}$, $R^{24}$ and $R^{25}$ are identical or different and have the meaning of $R^{11}$ given above, and are identical or different to the latter,
b denotes the number 1, 2, 3, 4 or 5,
d denotes the number 0, 1, 2, 3, 4 or 5,
c has the meaning of a given above, and is identical or different to the latter,
$R^{20}$ and $R^{21}$ are identical or different and denote aryl having from 6 to 10 carbon atoms which is optionally substituted up to 2 times by identical or different substituents comprising halogen, nitro, amino, hydroxyl or carboxyl or by straight-chain or branched alkyl, alkoxy or alkoxycarbonyl having in each case up to 6 carbon atoms, $R^{22}$ and $R^{23}$ are identical or different and denote hydrogen or a straight-chain, branched, saturated, unsaturated or cyclic hydrocarbon radical having up to 8 carbon atoms which is optionally substituted up to 2 times by identical or different substituents comprising hydroxyl, halogen or cycloalkyl having from 3 to 6 carbon atoms or by aryl or aryloxy having from 6 to 10 carbon atoms, which may in turn be substituted up to 2 times by identical or different substituents comprising halogen, nitro, amino, hydroxyl or carboxyl or by straight-chain or branched alkyl, alkoxy or alkoxycarbonyl having in each case up to 6 carbon atoms, or denote aryl having from 6 to 10 carbon atoms which is optionally substituted up to 2 times by identical or different substituents comprising halogen, nitro, amino, hydroxyl or carboxyl or by straight-chain or branched alkyl, alkoxy or alkoxycarbonyl having in each case up to 6 carbon atoms, or $R^{22}$ and $R^{23}$, together with the nitrogen atom, form a 5- to 7-membered saturated or unsaturated heterocycle having up to 3 heteroatoms from the series S, N or O, which is optionally substituted by straight-chain or branched alkyl having up to 4 carbon atoms which may in turn be substituted by phenyl, or is optionally substituted by phenyl which may in turn be substituted by halogen, or the hydrocarbon radical, in the case where A represents oxygen, is substituted by a 3- to 7-membered saturated or unsaturated heterocycle or heterocyclyloxy ring which may contain up to 3 heteroatoms from the series S, N or O, or groups of the formula —CO or —SO$_2$, where the heterocycle may in turn be substituted up to 2 times by identical or different substituents comprising halogen or hydroxyl or by aryl or arylsulphonyl having from 6 to 10 carbon atoms which may in turn be substituted up to 2 times by identical or different substituents comprising halogen, nitro, amino, hydroxyl or carboxyl or by straight-chain or branched alkyl, alkoxy or alkoxycarbonyl having in each case up to 6 carbon atoms, or the heterocycle is optionally substituted up to 2 times by identical or different substituents comprising straight-chain or branched alkyl, alkoxy or alkenyl having in each case up to 8 carbon atoms, which may in turn be substituted up to 2 times by identical or different groups —NR$^{26}$R$^{27}$, in which $R^{26}$ and $R^{27}$ have the meaning of $R^{22}$ and $R^{23}$ given above, and are identical or different to the latter, and all of the alkyl and alkenyl radicals are optionally substituted in turn by phenyl or phenoxy, which may in turn be substituted up to 2 times by identical or different substituents comprising halogen, nitro, amino, hydroxyl or carboxyl or by straight-chain or branched alkyl, alkoxy or alkoxycarbonyl having in each case up to 4 carbon atoms, $R^9$ and $R^{10}$ are identical or different and denote hydrogen, a straight-chain, branched, cyclic, saturated or unsaturated hydrocarbon radical having up to 8 carbon atoms which is optionally substituted by halogen, hydroxyl or cyano or by aryl, aryloxy or arylthio having in each case from 6 to 10 carbon atoms or by a 5- to 7-membered saturated or unsaturated heterocycle having up to 3 heteroatoms from the series S, N or O, the rings in turn possibly being substituted by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or denote aryl having from 6 to 10 carbon atoms or a 5- to 7-membered saturated or unsaturated heterocycle having up to 3 heteroatoms from the series S, N or O, which are optionally substituted up to 2 times by identical or different substituents comprising halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or $R^9$ and $R^{10}$, together and including the nitrogen atom, form a 3- to 8-membered saturated or unsaturated heterocycle which may optionally be interrupted by oxygen or by a radical of the formula S(O)$_e$, —CO— or —NR$^{28}$, in which e denotes the number 0, 1 or 2, $R^{28}$ denotes hydrogen or aryl having from 6 to 10 carbon atoms which is optionally substituted up to 2 times by identical or different substituents comprising halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or denotes a cyclic, straight-chain or branched hydrocarbon radical having up to 8 carbon atoms which is optionally substituted by hydroxyl or halogen or by aryl having from 6 to 10 carbon atoms or a 5- to 7-membered saturated or unsaturated heterocycle having 3 heteroatoms from the series S, N or O, which may in turn be substituted up to 2 times by identical or different substituents comprising halogen or cyano or by straight-chain or branched alkyl, alkoxy, alkylthio, alkoxycarbonyl, halogenoalkyl, halogenoalkoxy or halogenoalkylthio having in each case up to 4 carbon atoms, and which is optionally substituted by straight-chain or branched alkoxy or alkylthio having in each case up to 4 carbon atoms, halogen, aryl having from 6 to 10 carbon atoms, a 5- to 7-membered saturated or unsaturated heterocycle having up to 3 heteroatoms from the series S, N or O, or by straight-chain or branched alkyl having up to 4 carbon atoms which is optionally substituted in turn by aryl having from 6 to 10 carbon atoms, and salts thereof.

Possible physiologically acceptable salts are salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid and benzoic acid, or methanesulphonic acid, ethanesulphonic acid, phenylsulphonic acid, toluenesulphonic acid or naphthalenedisulphonic acid.

The compounds according to the invention exist in stereoisomeric forms which are either mirror images of one another (enantiomers) or otherwise (diastereomers). The invention relates both to the optical isomers and to the racemic forms, as well as to the mixtures of diastereomers. Both the racemic forms and the diastereomers can be separated in a known manner into the stereoisomerically uniform constituents (cf. E. L. Eliel, Stereochemistry of Carbon Compounds, McGraw Hill, 1962).

Preferred compounds of the general formula (I) are those in which $R^1$ and $R^5$ are identical or different and represent straight-chain or branched alkyl having up to 4 carbon atoms, $R^2$ represents nitro or cyano or $R^1$ and $R^2$ together form a lactone ring of the formula

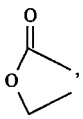

$R^6$ represents hydrogen, fluorine or chlorine, $R^3$ represents phenyl which is optionally substituted up to two times by fluorine, chlorine, bromine, nitro, cyano, hydroxyl or trifluoromethyl or by straight-chain or branched alkyl, alkoxy or alkoxycarbonyl having in each case up to 4 carbon atoms, or represents thienyl or pyridyl which are optionally substituted by fluorine, chlorine or bromine, $R^4$ represents cyano, nitro or formyl or $R^4$ and $R^5$ together form a lactone ring of the formula

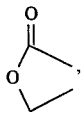

or $R^4$ represents a group of the formula —CO—A—$R^8$ or —CO—$NR^9R^{10}$ in which A denotes a direct bond or an oxygen atom, $R^8$ denotes cyclopropyl, cyclobutyl, cyclopentyl, cyclohexyl or cycloheptyl which are optionally interrupted by the group —$NR^{11}$, or denotes a straight-chain, branched, cyclic, saturated or unsaturated hydrocarbon radical having up to 10 carbon atoms which is optionally substituted by phenyl, and which is optionally interrupted by oxygen, phenylidene or by a group of the formula

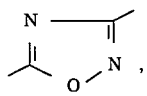

—$S(O)_a$ or —$NR^{11}$, in which a denotes the number 0, 1 or 2 and $R^{11}$ denotes hydrogen or phenyl which is optionally substituted by halogen, methyl, methoxy or nitro, or denotes cyclopropyl, cyclopentyl, cyclohexyl or straight-chain or branched alkyl having up to 5 carbon atoms which is optionally substituted by phenyl, and where the hydrocarbon radical, in the case where A represents oxygen, is always substituted by cyclopropyl, cyclobutyl, cyclopentyl or cyclohexyl or by a group —CO—$NR^{12}R^{13}$, —$NR^{14}$—CO—$R^{15}$, —$NR^{16}$—$SO_2$—$R^{17}$, —$SO_2$—$NR^{18}R^{19}$, O—$NO_2$, —O—$(CH_2)_b$—$R^{20}$, —$S(O)_c$—$(CH_2)_2$—$R^{21}$, —$NR^{22}R^{23}$ or —$NR^{24}$—$COOR^{25}$, in which $R^{12}$, $R^{13}$, $R^{14}$, $R^{15}$, $R^{16}$, $R^{17}$, $R^{18}$, $R^{19}$, $R^{24}$ and $R^{25}$ are identical or different and have the meaning of $R^{11}$ given above, and are identical or different to the latter, b denotes the number 1, 2, 3 or 4, d denotes the number 0, 1, 2, 3 or 4, c has the meaning of a given above, and is identical or different to the latter, $R^{20}$ and $R^{21}$ are identical or different and denote phenyl which is optionally substituted up to 2 times by identical or different substituents comprising fluorine, chlorine, bromine, nitro, hydroxyl or carboxyl or by straight-chain or branched alkyl, alkoxy or alkoxycarbonyl having in each case up to 4 carbon atoms, $R^{22}$ and $R^{23}$ are identical or different and denote hydrogen or a straight-chain, branched, saturated, unsaturated or cyclic hydrocarbon radical having up to 6 carbon atoms which is optionally substituted up to 2 times by identical or different substituents comprising fluorine, chlorine, cyclopropyl, cyclopentyl, cyclohexyl, phenyl or phenoxy, which may in turn be substituted by fluorine, chlorine, bromine, nitro, amino, hydroxyl or carboxyl or by straight-chain or branched alkyl, alkoxy or alkoxycarbonyl having in each case up to 4 carbon atoms, or denote phenyl which is optionally substituted by fluorine, chlorine, hydroxyl or carboxyl or by straight-chain or branched alkyl, alkoxy or alkoxycarbonyl having in each case up to 3 carbon atoms, or $R^{22}$ and $R^{23}$, together with the nitrogen atom, form a morpholine, piperidine or piperazine ring, which are optionally substituted by straight-chain or branched alkyl having up to 4 carbon atoms, phenyl or benzyl, or the hydrocarbon radical, in the case where A represents oxygen, is substituted by pyridyl, tetrahydropyranyl, pyrazolyl, furyl, chromanyl, piperazinyl, piperidyl or tetrahydroisoquinolidinyl or by a radical of the formula

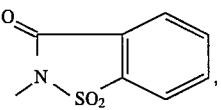 , 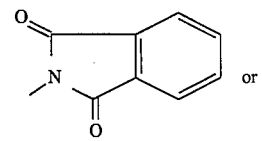 or

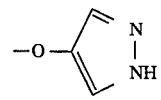

where the heterocycles may in turn be substituted by fluorine, chlorine or straight-chain or branched alkyl or alkoxy having in each case up to 3 carbon atoms or by phenyl, benzyl or phenylsulphonyl which may in turn be substituted by fluorine, chlorine, bromine, nitro, amino, hydroxyl or carboxyl or by straight-chain or branched alkyl, alkoxy or alkoxycarbonyl having in each case up to 3 carbon atoms, $R^9$ and $R^{10}$ are identical or different and denote hydrogen or a straight-chain, branched, cyclic, saturated or unsaturated hydrocarbon radical having up to 6 carbon atoms which is optionally substituted by fluorine, chlorine or phenyl, or denote phenyl which is optionally substituted by fluorine, chlorine, straight-chain or branched alkyl, alkoxy, alkylthio, alkoxycarbonyl having in each case up to 6 carbon atoms, trifluoromethyl or trifluoromethoxy, or $R^9$ and $R^{10}$, together and including the nitrogen atom, form a 5- to 6-membered saturated or unsaturated heterocycle which may optionally be interrupted by an oxygen atom or by a radical of the formula —$NR^{28}$, in which
- $R^{28}$ denotes hydrogen or phenyl or a cyclic, straight-chain or branched hydrocarbon radical having up to 6 carbon atoms, and salts thereof.

Particularly preferred compounds of the general formula (I) are those
in which
- $R^1$ and $R^5$ are identical or different and represent methyl or ethyl,
- $R^2$ represents nitro or cyano or
- $R^1$ and $R^2$ together form a lactone ring of the formula

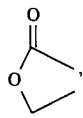

- $R^6$ represents hydrogen,
- $R^3$ represents phenyl which is optionally substituted by fluorine, chlorine, nitro, cyano, hydroxyl, trifluoromethyl, methyl, ethyl, methoxy or ethoxy,
- $R^4$ represents cyano, nitro or formyl or
- $R^4$ and $R^5$ together form a lactone ring of the formula

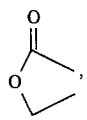

or
- $R^4$ represents a group of the formula —CO—A—$R^8$ or —CO—NR$^9$R$^{10}$ in which
- A denotes a direct bond or an oxygen atom,
- $R^8$ denotes cyclopropyl, cyclobutyl, cyclopentyl or cyclohexyl which are optionally interrupted by the group —NR$^{11}$, or denotes a straight-chain, branched, cyclic, saturated or unsaturated substituted hydrocarbon radical having up to 8 carbon atoms which is optionally interrupted by an oxygen atom, phenylidene or by a group of the formula —S(O)$_a$ or —NR$^{11}$ and is optionally substituted by phenyl, in which
- a denotes the number 0 or 2 and
- $R^{11}$ denotes hydrogen or phenyl which is optionally substituted by fluorine, chlorine, methyl or methoxy, or denotes cyclopropyl, cyclopentyl, cyclohexyl, or straight-chain or branched alkyl having up to 4 carbon atoms which is optionally substituted by phenyl,
- and where the hydrocarbon radical, in the case where A represents oxygen, is always substituted by cyclopropyl, cyclobutyl, cyclopentyl or cyclohexyl or by a group —CO—NR$^{12}$R$^{13}$, —NR$^{14}$—CO—R$^{15}$, —NR$^{16}$—SO$_2$—R$^{17}$, —SO$_2$—NR$^{18}$R$^{19}$, O—NO$_2$, —O—(CH$_2$)$_b$—R$^{20}$, —S(O)$_c$—(CH$_2$)$_d$—R$^{21}$, —NR$^{22}$R$^{23}$ or —NR$^{24}$—COOR$^{25}$, in which
- $R^{12}$, $R^{13}$, $R^{14}$, $R^{15}$, $R^{16}$, $R^{17}$, $R^{18}$, $R^{19}$, $R^{24}$ and $R^{25}$ are identical or different and have the meaning of $R^{11}$ given above, and are identical or different to the latter,

- b denotes the number 1, 2, 3 or 4,
- d denotes the number 0, 1, 2, 3 or 4,
- c has the meaning of a given above, and is identical or different to the latter,
- $R^{20}$ and $R^{21}$ are identical or different and denote phenyl which is optionally substituted by fluorine, chlorine, methyl or methoxy,
- $R^{22}$ and $R^{23}$ are identical or different and denote hydrogen or a straight-chain, branched, saturated, unsaturated or cyclic hydrocarbon radical having up to 4 carbon atoms which is optionally substituted by fluorine, chlorine, cyclopropyl, cyclopentyl, cyclohexyl, phenyl or phenoxy, which may in turn be substituted by fluorine, chlorine or hydroxyl or by methyl or methoxy, or denote phenyl which is optionally substituted by fluorine, chlorine, methyl or methoxy, or
- $R^{22}$ and $R^{23}$, together with the nitrogen atom, form a piperidine or piperazine ring, which is optionally substituted by benzyl, or the hydrocarbon radical, in the case where A represents oxygen, is substituted by pyridyl, tetrahydropyranyl, pyrazolyl, furyl, chromanyl, piperazinyl, piperidyl or isoquinolidinyl or by a radical of the formula

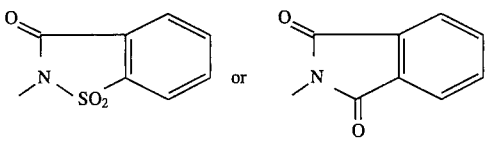

- $R^9$ and $R^{10}$ are identical or different and denote hydrogen, a straight-chain, branched, cyclic, saturated or unsaturated hydrocarbon radical having up to 6 carbon atoms which may optionally be substituted by phenyl, or denote phenyl or pyridyl, and salts thereof.

Very particularly preferred compounds of the general formula (I) are those
in which
- $R^1$ and $R^5$ represent methyl,
- $R^2$ represents cyano or nitro or
- $R^1$ and $R^2$ together form a lactone ring of the formula

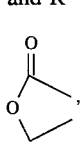

- $R^6$ represents hydrogen and
- $R^3$ represents phenyl which is optionally substituted by fluorine, chlorine, hydroxyl, methyl or methoxy,
- $R^4$ represents a radical of the formula —CO—A—$R^8$ or —CO—NR$^9$R$^{10}$, in which
- A denotes a direct bond or an oxygen atom,
- $R^8$ denotes cyclopropyl, cyclobutyl, cyclopentyl or cyclohexyl which are optionally interrupted by the group —NR$^{11}$, or denotes a straight-chain, branched, cyclic, saturated or unsaturated substituted hydrocarbon radical having up to 6 carbon atoms which is optionally interrupted by an oxygen or sulphur atom or the group —NR$^{11}$, in which R$^{11}$ denotes methyl, phenyl or benzyl, and where the hydrocarbon radical, in the case where A represents oxygen, is always substituted by pyridyl, cyclopropyl, cyclobutyl, cyclopentyl or cyclohexyl or by a group —NR$^{14}$—CO—R$^{15}$, —NR$^{16}$—SO$_2$—R$^{17}$, —O—(CH$_2$)$_b$—R$^{20}$, —NR$^{22}$R$^{23}$, —NR$^{24}$—COOR$^{25}$,

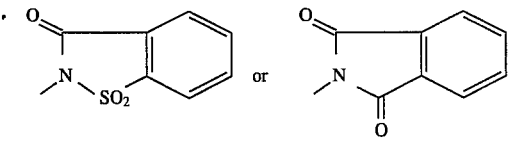

in which

R$^{14}$, R$^{15}$, R$^{16}$, R$^{17}$, R$^{24}$ and R$^{25}$ are identical or different and denote hydrogen or phenyl which is optionally substituted by fluorine, chlorine, methyl or methoxy, or denote straight-chain or branched alkyl having up to 4 carbon atoms which is optionally substituted by phenyl, b denotes the number 1 or 2, R$^{20}$ denotes phenyl which is optionally substituted by methyl or methoxy, R$^{22}$ and R$^{23}$ are identical or different and denote hydrogen, phenyl or a straight-chain or branched hydrocarbon radical having up to 4 carbon atoms which is optionally substituted by cyclopropyl, cyclopentyl, cyclohexyl, phenyl or phenoxy, which may in turn be substituted by hydroxyl, methyl or methoxy, or R$^{22}$ and R$^{23}$, together with the nitrogen atom, form a piperidine ring which is optionally substituted by benzyl, R$^9$ and R$^{10}$ are identical or different and denote hydrogen, cyclopropyl or straight-chain or branched alkyl having up to 4 carbon atoms, and salts thereof.

The process for the preparation of the compounds of the general formula (I) according to the invention is characterized in that, in the case where R$^1$ and R$^2$ have the meaning given above but do not together form a lactone ring,

[A] compounds of the general formula (II)

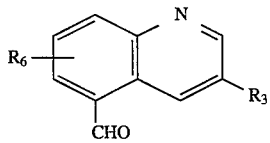 (II)

in which

R$^3$ and R$^6$ have the meaning given above are reacted first with acyl derivatives of the general formula (III)

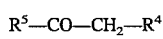 (III)

in which

R$^4$ and R$^5$ have the meaning given above, with the optional isolation of the corresponding ylidene compounds of the general formula (IV)

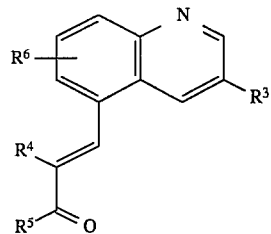 (IV)

in which

R$^3$, R$^4$, R$^5$ and R$^6$ have the meaning given above, and then the product is reacted either with compounds of the formula (V)

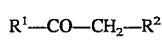 (V)

in which

R$^1$ and R$^2$ have the meaning given above in the presence of ammonia or ammonium salts, or directly with amino derivatives of the general formula (VI)

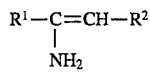 (VI)

in which

R$^1$ and R$^2$ have the meaning given above, optionally in the presence of inert organic solvents, or

[B] the aldehydes of the general formula (II) are reacted first with the compounds of the general formula (V), with the optional isolation of the ylidene compounds of the general formula (VII)

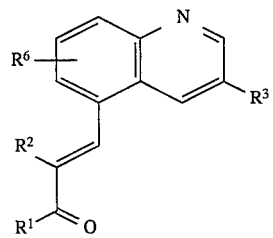 (VII)

in which

R$^1$, R$^2$, R$^3$ and R$^6$ have the meaning given above, and, in a subsequent step, the product is reacted with the abovementioned compounds of the general formula (III) in inert solvents, in the presence of ammonia or ammonium salts or directly with enamino acid derivatives of the general formula (VIII)

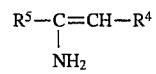 (VIII)

in which

R$^4$ and R$^5$ have the meaning given above, or, in the case where R$^1$ and R$^2$ together form a lactone ring,

[C] according to the methods given under [A] and [B], compounds of the general formula (IX)

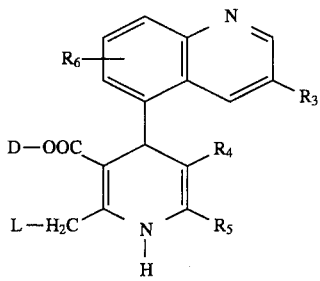

(IX)

in which

R$^3$, R$^4$, R$^5$ and R$^6$ have the meaning given above,

D represents a C$_1$–C$_6$-alkyl radical and

L represents a leaving group such as, for example, chlorine or acetoxy, are first prepared, and subsequently an acid- or base-catalysed cyclization is carried out by known methods, or

[D] in the case where R$^4$ represents the radical of the formula —CO—A—R$^8$ (A=oxygen) or —CO—NR$^9$R$^{10}$, compounds of the general formula (X)

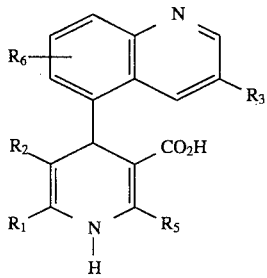

(X)

in which

R$^1$, R$^2$, R$^3$, R$^5$ and R$^6$ have the meaning given above are reacted, optionally via a reactive acid derivative, with alcohols or amines of the general formula (XI) or (XII)

HA—R$^8$   (XI)

or

HNR$^9$R$^{10}$   (XII)

in which

A, R$^8$, R$^9$ and R$^{10}$ have the meaning given above, in which case, if chiral carboxylic acids are employed, the corresponding chiral esters or amides are obtained.

The processes according to the invention can be illustrated by the following scheme:

[A]

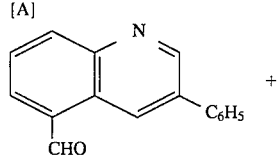

+

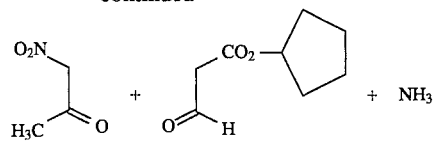

+ NH$_3$

↓

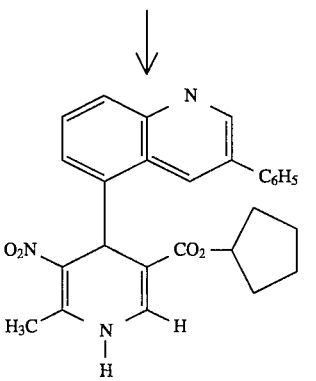

[B]

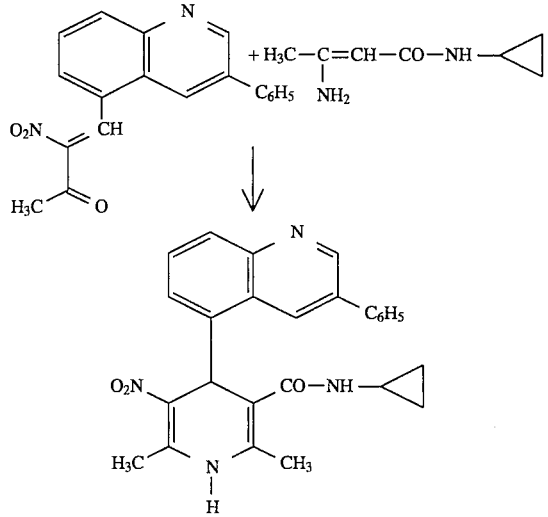

[C]

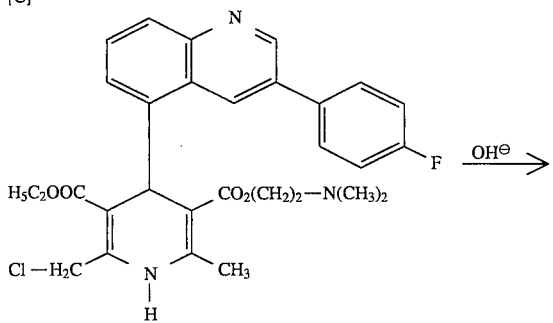

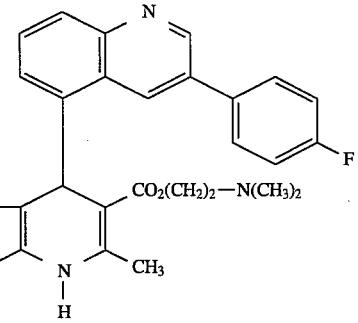

[D]

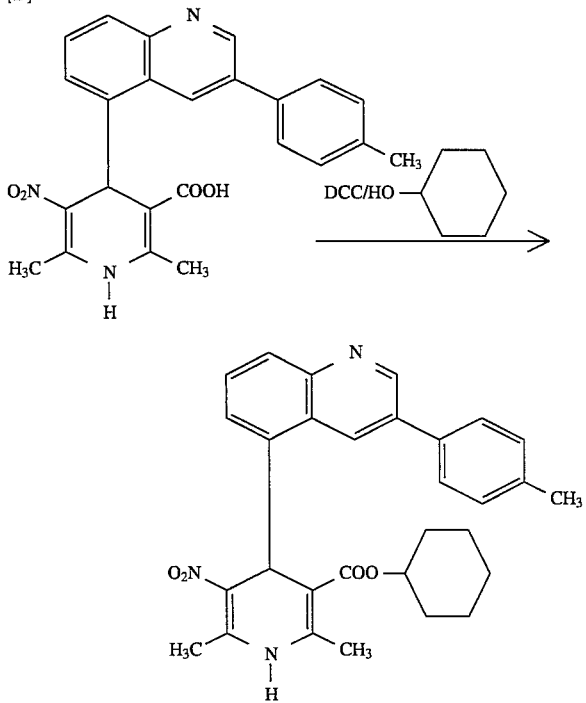

Suitable solvents for processes [A], [B] and [C] are all inert organic solvents, preferred among these solvents are alcohols such as methanol, ethanol, n- or iso-propanol, ethers such as diethyl ether, tetrahydrofuran, dioxane or glycol mono- or dimethyl ether, glacial acetic acid, pyridine, dimethylformamide, dimethyl sulphoxide, acetonitrile or hexamethylphosphoric triamide or toluene.

Suitable solvents for process [D] are the solvents listed above with the exception of the alcohols.

The reaction temperatures for processes [A], [B], [C] and [D] can be varied within a relatively wide range. They are in general carried out in a range from 10° C. to 200° C., preferably from 20° C. to 150° C.

The processes can be carried out at atmospheric pressure or under increased or reduced pressure (for example from 0.5 to 5 bar), preferably at atmospheric pressure.

When carrying out the processes according to the invention, the ratio of the substances taking part in the reaction is not critical. In general, however, molar quantities of the reactants are used.

Suitable reagents for activating the carboxylic acid are those which are conventional, such as inorganic halides, for example thionyl chloride, phosphorus trichloride or phosphorus pentachloride or carbonyldiimidazole, carbodiimides such as cyclohexylcarbodiimide or 1-cyclohexyl-3-[2-(N-methylmorpholino)ethyl]-carbodiimide p-toluenesulphonate or N-hydroxyphthalimide or N-hydroxy-benzotriazole.

Enantiomerically pure forms are obtained by, for example, separating diastereomer mixtures of the compounds of the general formula (I), in which $R^4$ represents an optical ester radical, by conventional methods, subsequently preparing the enantiomerically pure carboxylic acids and then, for example by esterification with corresponding alcohols, performing conversion into the enantiomerically pure dihydropyridinecarboxylic acid esters.

Suitable chiral ester radicals are all esters of enantiomerically pure alochols such as, for example, 2-butanol, 1-phenylethanol, lactic acid, lactic acid esters, mandelic acid, mandelic acid esters, 2-amino-alcohols, sugar derivatives and many other enantiomerically pure alcohols.

The diastereomers are separated in general either by fractional crystallization, by column chromatography or by Craig partition. Which method is the optimum must be decided from case to case; sometimes it is also expedient to use combinations of the individual methods. A particularly suitable separation involves crystallization or Craig partition or a combination of the two methods.

The esterification of the enantiomerically pure dihydropyridines is preferably carried out in ethers such as diethyl ether or tetrahydrofuran, dimethylformamide, methylene chloride, chloroform, acetonitrile or toluene.

The aldehydes of the general formula (II) are known or can be prepared by conventional methods (U.S. Pat. No. 5,100,900).

In addition, the acyl derivatives of the formula (III), the ylidene compounds (IV) and (VII), and the enamino derivatives of the formula (VI) and (VIII) are known or can be prepared by conventional methods.

The preceding preparation processes are given only by way of clarification. The preparation of the compounds of the formula (I) is not restricted to these processes; rather, any modification of these processes can be employed in the same manner for the preparation of the compounds according to the invention.

The compounds according to the invention exhibit an unforeseeable and valuable spectrum of pharmacological action. They influence myocardial contractility and smooth-muscle tone. They particularly have a positively inotropic action.

They can therefore be employed in pharmaceuticals for influencing pathologically altered blood pressure, in coronary therapy, and for treating cardiac insufficiency. They can also be used for treating cardiac arrhythmias, for reducing blood sugar, for decongesting the mucosae and for influencing the salt and fluid balance.

The cardiac and vascular actions were demonstrated on the guinea-pig heart perfused in isolation. For this purpose, the hearts of guinea pigs weighing from 250 to 350 g are used. The animals are sacrificed by a blow to the head, the thorax is opened, and a metal cannula is inserted and attached in the exposed aorta. The heart and the lungs are excised from the thorax and connected, via an aortic cannula, to the perfusion apparatus in the course of perfusion. The lungs are separated at the roots. The perfusion medium used is a Krebs-Henseleit solution (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$ and 0,013 mmol/l of $Na_2EDTA$) with a $CaCl_2$ content of 1.2 mmol/l. The energy-supplying substrate added is glucose at 10 mmol/l. Prior to the perfusion, the solution is filtered to remove all particles. The solution is gassed with carbogen (95% $O_2$, 5% $CO_2$) to maintain a pH of 7.4. The hearts are perfused at 32° C. at a constant flow rate (10 ml/min) using a peristaltic pump.

For measuring the cardiac function, a liquid-filled latex balloon which is connected via a liquid column to a pressure transducer is inserted through the left atrium into the left ventricle, and the isovolumetric contractions are recorded on a rapid recorder. The perfusion pressure is recorded using a pressure transducer which is connected to the perfusion system upstream of the heart.

Under these conditions, a reduction in the perfusion pressure indicates a coronary dilatation, and an increase or decrease in the amplitude of contraction in the left ventricle indicates a fall or rise, respectively, in myocardial contractility. The compounds according to the invention, in suitable dilutions, are introduced into the perfusion system a short distance upstream of the isolated heart.

The new compounds can be converted by known methods into the conventional formulations such as coated and uncoated tablets, pills, granules, aerosols, syrups, emulsions, suspensions and solutions, using inert, non-toxic, pharmaceutically appropriate excipients or solvents. In this context, the therapeutically active compound should in each case be present in a concentration of from approximately 0.5 to 90% by weight of the total mixture, i.e. in amounts sufficient to achieve the stated scope of dosage.

The formulations are prepared by, for example, extending the active compounds using solvents and/or excipients, with the optional use of emulsifiers and/or dispersants; where water is used as a diluent, organic solvents may optionally be used as auxiliary solvents.

Administration is made in a conventional manner, preferably orally or parenterally and, in particular, perlingually or intravenously.

It has in general proved advantageous, in the case of intravenous administration, to administer amounts of from approximately 0.001 to 1 mg/kg, preferably from approximately 0.01 to 0.5 mg/kg of body weight in order to achieve effective results; in the case of oral administration, the dosage is from approximately 0.01 to 20 mg/kg, preferably from 0.1 to 10 mg/kg of body weight.

Despite this, it may be necessary to depart from the stated amounts, specifically in dependence on the body weight or on the nature of the application route, on the individual response to the medicament, on the nature of its formulation and on the time at or over which administration is made. For instance, it may in some cases be sufficient to use less than the minimum amount stated above, while in other cases the upper limit mentioned has to be exceeded. In the case where greater quantities are administered, it may be advisable to distribute these in two or more individual doses over the day.

EXAMPLE 1

2-(N-Benzyl-N-methylamino)ethyl
2-methyl-4-[3-(4-methylphenyl)-5-quinolyl]-5-oxo-
1,4,5,7-tetrahydrofuro[3,4-b]pyridine-3-carboxylate

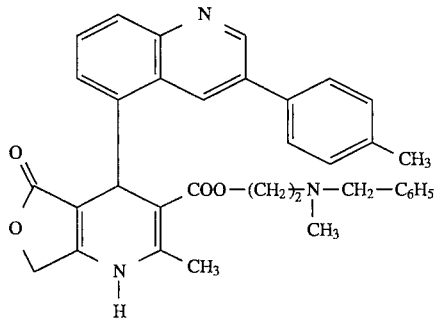

1.24 g (5 mmol) of 2-(N-benzyl-4-methylamino)-ethyl 3-aminocrotonate are added to 2.3 g (5.5 mmol) of ethyl 2-[3-(4-methylphenyl)-5-quinolylidene)]-4-acetoxy-3-oxo-butyrate in 30 ml of isopropanol, and the mixture is heated at reflux for 24 hours. It is cooled, concentrated and purified roughly by flash chromatography, affording 2.3 g of a prepurified oil. This oil is heated at reflux for 30 minutes in a mixture of 1 g of potassiumhydroxide in 40 ml of isopropanol. It is cooled, adjusted to neutral with 1N hydrochloric acid and concentrated, and the residue is taken up in ethyl acetate/water. The phases are separated and the ethyl acetate phase is washed with water, dried and concentrated. The crude product obtained is purified on a silica gel column using toluene/ethyl acetate mixtures. The pure fractions are collected, concentrated and crystallized from methanol. 550 mg of colourless crystals with a melting point of 173°–175° C. are obtained.

EXAMPLE 2

2,6-Dimethyl-3-nitro-4-(3-phenyl-5-quinolyl)-1,4-dihydropyridine-5-(N-cyclopropyl)-carboxamide

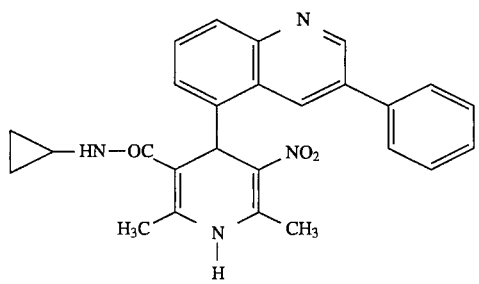

1.4 g (10 mmol) of N-cyclopropyl-3-aminocrotonamide, 1.8 g (17.5 mmol) of nitroacetone and 0.6 ml (10 mmol) of acetic acid are added to 2.33 g (10 mmol) of 3-phenyl-quinoline-5-carbaldehyde in 40 ml of ethanol, and the mixture is heated at reflux for 4 hours. It is cooled and concentrated and the residue is dissolved in ethyl acetate. The ethyl acetate solution is washed with water, sodium hydrogen carbonate solution and again with water, dried and concentrated. It is purified on a silica gel column using ethyl acetate/toluene mixtures. The pure fractions are combined and concentrated and the residue is crystallized from ethanol. 420 mg of yellow crystals with a melting point of 179°–182° C. are obtained.

The compounds listed in Tables 1 and 2 are prepared in analogy to the procedures of Examples 1 and 2:

TABLE 1

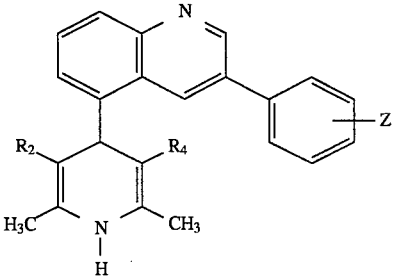

| Ex. No. | R² | R⁴ | Z | F°C. | Enantiomer |
|---|---|---|---|---|---|
| 3 | —CN | —CO₂—(CH₂)₅—NH₂ | H | 138 | |
| 4 | —CN | —CO—CH₃ | H | 244–249 | |
| 5 | —CN | —CO₂—(CH₂)₂—NH₂ | H | 217(decomp.) | |
| 6 | —CN | —CO₂—(CH₂)₅—N(phthalimido) | H | 118 | |
| 7 | —CN | —CO₂—(CH₂)₂—N(phthalimido) | H | 168 | |
| 8 | —CN | —CO—HN—cyclopropyl | H | 202 | |
| 9 | —CN | —CO₂—(CH₂)₂—N(CH₃)—CH₂—C₆H₅ | p-F | 186 | |
| 10 | —CN | —CO₂—(CH₂)₂—(3-pyridyl) | o-Cl | 199 | |
| 11 | —CN | —CO₂—(CH₂)₂—N⁺(CH₃)₂(CH₂C₆H₅) I⁻ | H | foam | |
| 12 | —CN | —CO₂—(CH₂)₂—N⁺(CH₃)₂(CH₂C₆H₅) I⁻ | H | foam | |
| 13 | —CN | —CO₂—(CH₂)₂—N(CH₃)(CH₂C₆H₅) | o-F | 157 | |
| 14 | —CN | —CO₂—(CH₂)₂—(3-pyridyl) | H | 159 | |
| 15 | —CN | —CO₂—(CH₂)₂—N(CH₃)(CH₂C₆H₅) | H | foam | (+) |
| 16 | —CN | —CO₂—(CH₂)₂—N(CH₃)(CH₂C₆H₅) | H | foam | |
| 17 | —CN | —CO₂—(CH₂)₂—N(CH₃)(CH₂C₆H₅) | H | 195 | |
| 18 | —NO₂ | —CO—CH₃ | H | 284 | |
| 19 | —NO₂ | —CO₂—(CH₂)₂—N(CH₃)(CH₂C₆H₅) | H | 220 | |

TABLE 1-continued
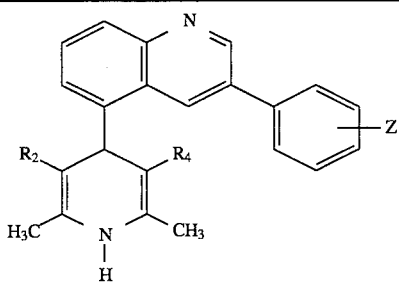
| Ex. No. | R² | R⁴ | Z | F°C. | Enantiomer |
|---|---|---|---|---|---|
| 20 | CN |  | H | 167–168 | |
TABLE 2
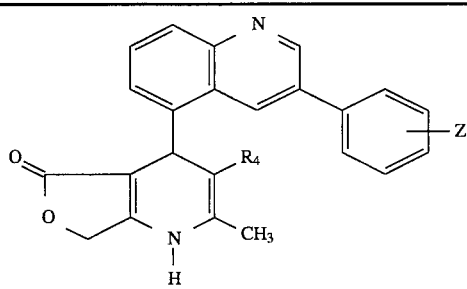
| Ex. No. | R⁴ | Z | F°C. | Enantiomer |
|---|---|---|---|---|
| 21 | —CONH—CH₃ | H | | |
| 22 | —CO—NH—C₂H₅ | H | 190 | |
| 23 | —CO—HN—⊲ | H | 202–204 | |
| 24 | —CO₂—(CH₂)₂—N(piperidine) | H | 210–212 | |
| 25 | —CO₂—(CH₂)₂—N(CH₃)₂ | H | 239–240 | |
| 26 | —CO₂—(piperidine)N—CH₂—C₆H₅ | p-CH₃ | 160(decomp) | |
| 27 | —CO₂—(CH₂)₂—N(CH₃)(CH₂C₆H₅) | H | 176 | |
| 28 | —CO₂—(CH₂)₂—(2-pyridyl) | H | 172 | |
| 29 | —CO₂—H₂C—(2-pyridyl) | H | 262 | |

TABLE 2-continued

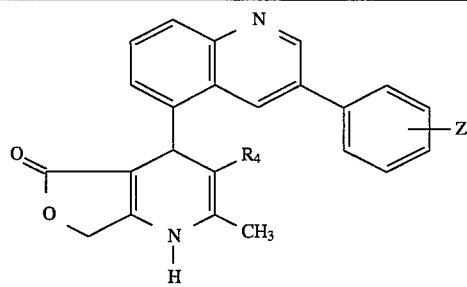

| Ex. No. | R⁴ | Z | F°C. | Enantiomer |
|---|---|---|---|---|
| 30 | —CO₂—⟨cyclohexyl-N—CH₂—C₆H₅⟩ | H | 223–230 | |
| 31 | —CO₂—(CH₂)₂—N(CH₃)—CH₂—C₆H₅ | m-OCH₃ | 169–172 | |
| 32 | —CO₂—(CH₂)₆—N(phthalimide) | H | 235(decomp.) | |
| 33 | —CO₂—cyclopentyl | p-F | >280 | |
| 34 | —CO₂—(CH₂)₂—N(CH₃)—CH₂—C₆H₅ | p-F | 169–170 | |
| 35 | —CO₂—(H₂C)₆—N(phthalimide) | m-OCH₃ | foam | |
| 36 | —COO—(CH₂)₂—NH—COO—CH₂—C₆H₅ | H | 142–144 | |
| 37 | —CO₂—(H₂C)₂—HN—O₂S—C₆H₅ | H | 214–216 | |

We claim:

1. A 4-quinolyl-dihydropyridine ester of the formula

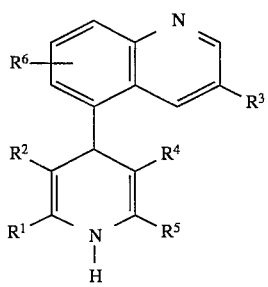 (I)

wherein $R^1$ and $R^5$ are identical or different and represent methyl or ethyl, $R^2$ represents nitro or cyano or $R^1$ and $R^2$ together form a lactone ring of the formula

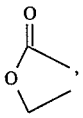, $R^6$ represents hydrogen, $R^3$ represents phenyl which is optionally substituted by fluorine, chlorine, nitro, cyano, hydroxyl, trifluoromethyl, methyl, ethyl, methoxy or ethoxy, $R^4$ represents cyano, nitro or formyl, or R⁴ and R⁵ together form a lactone ring of the formula

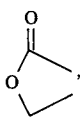

or

R⁴ represents a group of the formula —CO—A—R⁸ or —CO—NR⁹R¹⁰ in which

A denotes a direct bond or an oxygen atom,

R⁸ denotes cyclopropyl, cyclobutyl, cyclopentyl or cyclohexyl which are optionally interrupted by the group —NR¹¹, or denotes a straight-chain, branched, cyclic, saturated or unsaturated substituted hydrocarbon radical having up to 8 carbon atoms which is optionally interrupted by an oxygen atom, phenylidene or by a group of the formula —S(O)$_a$ or —NR¹¹ and is optionally substituted by phenyl, in which a denotes the number 0 or 2 and

R¹¹ denotes hydrogen or phenyl which is optionally substituted by fluorine, chlorine, methyl or methoxy, or denotes cyclopropyl, cyclopentyl, cyclohexyl, or straight-chain or branched alkyl having up to 4 carbon atoms which is optionally substituted by phenyl, and where the hydrocarbon radical, in the case where A represents oxygen, is always substituted by cyclopropyl, cyclobutyl, cyclopentyl or cyclohexyl or by a group —CO—NR¹²R¹³, —NR¹⁴—CO—R¹⁵, —NR¹⁶—SO₂—R¹⁷, —SO₂—NR¹⁸R¹⁹, O—NO₂, —O—(CH₂)$_b$—R²⁰, —S(O)$_c$—(CH₂)₄—R²¹, —NR²²R²³ or —NR²⁴—COOR²⁵, in which R¹², R¹³, R¹⁴, R¹⁵, R¹⁶, R¹⁷, R¹⁸, R¹⁹, R²⁴ and R²⁵ are identical or different and have the meaning of R¹¹ given above, and are identical or different to the latter, b denotes the number 1, 2, 3 or 4, d denotes the number 0, 1, 2, 3 or 4, c has the meaning of a given above, and is identical or different to the latter, R²⁰ and R²¹ are identical or different and denote phenyl which is optionally substituted by fluorine, chlorine, methyl or methoxy, R²² and R²³ are identical or different and denote hydrogen or a straight-chain, branched, saturated, unsaturated or cyclic hydrocarbon radical having up to 4 carbon atoms which is optionally substituted by fluorine, chlorine, cyclopropyl, cyclopentyl, cyclohexyl, phenyl or phenoxy, which are optionally substitute by fluorine, chlorine, methyl or methoxy, or R²² and R²³, together with the nitrogen atom, form a piperidine or piperazine ring, which is optionally substituted by benzyl, or the hydrocarbon radical, in the case where A represents oxygen, is substituted by pyridyl, tetrahydropyranyl, pyrazolyl, furyl, or chromanyl, or by a radical of the formula

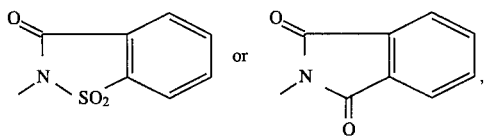

R⁹ and R¹⁰ are identical or different and denote hydrogen, a straight-chain, branched, cyclic, saturated or unsaturated hydrocarbon radical having up to 6 carbon atoms which may optionally be substituted by phenol, or denote phenyl or pyridyl, or a pharmaceutically acceptable salt thereof.

2. A compound according to claim 1, wherein

R¹ and R⁵ are identical or different and represent methyl or ethyl,

R² represents nitro or cyano or

R¹ and R² together form a lactone ring of the formula

R⁶ represents hydrogen,

R³ represents phenyl which is optionally substituted by fluorine, chlorine, nitro, cyano, hydroxyl, trifluoromethyl, methyl, ethyl, methoxy or ethoxy, R⁴ represents cyano, nitro or formyl R⁴ represents a group of the formula —CO—A—R⁸ or —CO—NR⁹R¹⁰ in which

A denotes a direct bond or an oxygen atom,

R⁸ denotes cyclopropyl, cyclobutyl, cyclopentyl or cyclohexyl which are optionally interrupted by the group —NR¹¹, or denotes a straight-chain, branched, cyclic, saturated or unsaturated substituted hydrocarbon radical having up to 8 carbon atoms which is optionally interrupted by an oxygen atom, phenylidene or by a group of the formula —S(O)$_a$ or —NR¹¹ and is optionally substituted by phenyl, in which a denotes the number 0 or 2 and

R¹¹ denotes hydrogen or phenyl which is optionally substituted by fluorine, chlorine, methyl or methoxy, or denotes cyclopropyl, cyclopentyl, cyclohexyl, or straight-chain or branched alkyl having up to 4 carbon atoms which is optionally substituted by phenyl, and where the hydrocarbon radical, in the case where A represents oxygen, is always substituted by cyclopropyl, cyclobutyl, cyclopentyl or cyclohexyl or by a group —CO—NR¹²R¹³, —NR¹⁴—CO—R¹⁵, —NR¹⁶—SO₂—R¹⁷, —SO₂—NR¹⁸R¹⁹, O—NO₂, —O—(CH₂)$_b$—R²⁰, —S(O)$_c$—(CH₂)$_d$—R²¹, —NR²²R²³ or —NR²⁴—COOR²⁵, in which R¹², R¹³, R¹⁴, R¹⁵, R¹⁶, R¹⁷, R¹⁸, R¹⁹, R²⁴ and R²⁵ are identical or different and have the meaning of R¹¹ given above, and are identical or different to the latter, b denotes the number 1, 2, 3 or 4, d denotes the number 0, 1, 2, 3 or 4, c has the meaning of a given above, and is identical or different to the latter, R²⁰ and R²¹ are identical or different and denote phenyl which is optionally substituted by fluorine, chlorine, methyl or methoxy, $R^{22}$ and $R^{23}$ are identical or different and denote hydrogen or a straight-chain, branched, saturated, unsaturated or cyclic hydrocarbon radical having up to 4 carbon atoms which is optionally substituted by fluorine, chlorine, cyclopropyl, cyclopentyl, cyclohexyl, phenyl or phenoxy, which are optionally substitute by fluorine, chlorine, methyl or methoxy, $R^9$ and $R^{10}$ are identical or different and denote hydrogen, a straight-chain, branched, cyclic, saturated or unsaturated hydrocarbon radical having up to 6 carbon atoms which may optionally be substituted by phenyl, or denote phenyl or a pharmaceutically acceptable salt thereof.

3. A compound according to claim 1, in which $R^1$ and $R^5$ represent methyl, $R^2$ represents nitro or cyano, or $R^1$ and $R^2$ together form a lactone ring of the formula

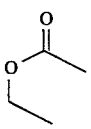

$R^6$ represents hydrogen, $R^3$ represents phenyl which is optionally substituted by fluorine, chlorine, nitro, cyano, hydroxyl, trifluoromethyl, methyl, ethyl, methoxy or ethoxy, $R^4$ represents cyano, nitro or formyl, or $R^4$ and $R^5$ together form a lactone ring of the formula

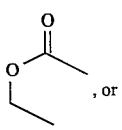

$R^4$ represents a group of the formula —CO—A—$R^8$ or —CO—NR$^9$R$^{10}$, in which A denotes a direct bond or an oxygen atom $R^8$ denotes cyclopropyl, cyclobutyl, cyclopentyl or cyclohexyl which are optionally interrupted by the group —NR$^{11}$, or denotes a straight-chain, branched, cyclic, saturated or unsaturated substituent hydrocarbon radical having up to 8 carbon atoms which is optionally interrupted by an oxygen atom, phenylidene or by a group of the formula —S(O)$_a$ or —NR$^{11}$ and is optionally substituted by phenyl, in which a denotes the number 0 or 2 and $R^{11}$ denotes hydrogen or phonyl which is optionally substituted by fluorine, chlorine, methyl or methoxy, or denotes cyclopropyl, cyclopentyl, cyclohexyl or straight-chain or branched alkyl having up to 4 carbon atoms which is optionally substituted by phenyl, and where the hydrocarbon radical, in these where A represents oxygen, is always substituted by pyridyl, cyclopropyl, cyclobutyl, cyclopentyl or cyclohexyl or by a group —NR$^{14}$—CO—R$^{15}$, —NR$^{16}$—SO$_2$—R$^7$, —O—(CH$_2$)$_b$—R$^{20}$, —NR$^{22}$R$^{23}$, —NR$^{24}$—COOR$^{25}$,

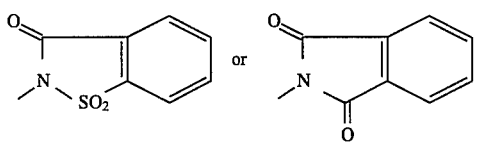

in which $R^{14}$, $R^{15}$, $R^{16}$, $R^{17}$, $R^{24}$ and $R^{25}$ are identical or different and denote hydrogen or phenyl which is optionally substituted by fluorine, chlorine, methyl or methoxy, or denote straight-chain or branched alkyl having up to 4 carbon atoms which is optionally substituted by phenyl, b denotes the number 1 or 2, $R^{20}$ denotes phenyl which is optionally substituted by methyl or methoxy, $R^{22}$ and $R^{23}$ are identical or different and denote hydrogen, phenyl or a straight-chain or branched hydrocarbon radical having up to 4 carbon atoms which is optionally substituted by cyloopropyl, cyclopentyl, cyclohexyl, phenyl or phenoxy, which may in turn be substituted by hydroxyl, methyl or methoxy, or $R^{22}$ and $R^{23}$ together with the nitrogen atom, for a piperidine ring which is optionally substituted by benzyl, $R^9$ and $R^{10}$ are identical or different and denote hydrogen, cyclopropyl or straight-chain or branched alkyl having up to 4 carbon atoms, or a pharmaceutically acceptable salt thereof.

4. A compound according to claim 1, wherein $R^1$ and $R^5$ represent methyl, $R^2$ represents cyano or nitro or $R^1$ and $R^2$ together form a lactone ring of the formula

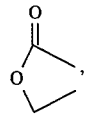

$R^6$ represents hydrogen and $R^3$ represents phenyl which is optionally substituted by fluorine, chlorine, hydroxyl, methyl or methoxy, $R^4$ represents a radical of the formula —CO—A—$R^8$ or —CO—NR$^9$R$^{10}$, in which A denotes a direct bond or an oxygen atom, $R^8$ denotes cyclopropyl, cyclobutyl, cyclopentyl or cyclohexyl which are optionally interrupted by the group —NR$^{11}$, or denotes a straight-chain, branched, cyclic, saturated or unsaturated substituted hydrocarbon radical having up to 6 carbon atoms which is optionally interrupted by an oxygen or sulphur atom or the group —NR$^{11}$, in which $R^{11}$ denotes methyl, phenyl or benzyl, and where the hydrocarbon radical, in the case where A represents oxygen, is always substituted by pyridyl, cyclopropyl, cyclobutyl, cyclopentyl or cyclohexyl or by a group —NR$^{14}$—CO—R$^{15}$, —NR$^{16}$—SO$_2$—R$^{17}$, —O—(CH$_2$)$_b$—R$^{20}$, —NR$^{22}$R$^{23}$, or —NR$^{24}$—COOR$^{25}$,

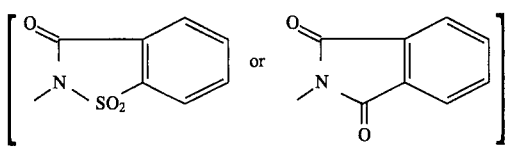

in which

R$^{14}$, R$^{15}$, R$^{16}$, R$^{17}$, R$^{24}$ and R$^{25}$ are identical or different and denote hydrogen or phenyl which is optionally substituted by fluorine, chlorine, methyl or methoxy, or denote straight-chain or branched alkyl having up to 4 carbon atoms which is optionally substituted by phenyl, b denotes the number 1 or 2, R$^{20}$ denotes phenyl which is optionally substituted by methyl or methoxy, R$^{22}$ and R$^{23}$ are identical or different and denote hydrogen, phenyl straight-chain or branched hydrocarbon radical having up to 4 carbon atoms which is optionally substituted by cyclopropyl, cyclopentyl, cyclohexyl, phenyl or phenoxy, which in turn are optionally substituted by hydroxyl, methyl or methoxy, or R$^9$ and R$^{10}$ are identical or different and denote hydrogen, cyclopropyl or straight-chain or branched alkyl having up to 4 carbon atoms, or a pharmaceutically acceptable salt thereof.

5. A compound according to claim 1 which is 2-(N-Benzyl-N-methylamino)ethyl 2-methyl-4-[3-(4-methylphenyl)-5-quinolyl]-5-oxo-1,4,5,7-tetrahydrofuro[3,4-b]-pyridine-3-carboxylate.

6. A pharmaceutical composition comprising a compound according to claim 1 and inert carrier.

7. A method of treating cardiac circulatory disorders which comprises administering a compound according to claim 1 to a host in need therefor.

* * * * *

UNITED STATES PATENT AND TRADEMARK OFFICE
CERTIFICATE OF CORRECTION

PATENT NO. : 5,508,406
DATED     : April 16, 1996
INVENTOR(S) : Stoltefuss, et al.

It is certified that error appears in the above-indentified patent and that said Letters Patent is hereby corrected as shown below:

Col. 23, line 37     Delete " $-S(O)_c-(CH_2)_4-R^{21}$ " and substitute -- $-S(O)_c-(CH_2)_d-R^{21}$ --

Col. 24, line 11     Delete " phenol " and substitute -- phenyl --

Col. 25, line 57     Delete " phonyl " and substitute -- phenyl --

Col. 27, lines 1-    Delete " 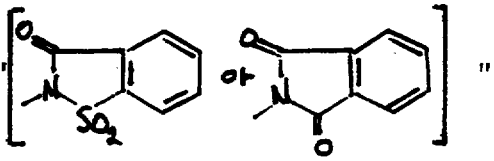 "

Signed and Sealed this

First Day of October, 1996

Attest:

BRUCE LEHMAN

Attesting Officer       Commissioner of Patents and Trademarks